United States Patent
Li

(10) Patent No.: US 10,605,815 B2
(45) Date of Patent: Mar. 31, 2020

(54) FULLY-AUTOMATIC EXCREMENT ANALYZER

(71) Applicant: Suzhou Halo Bio-Tech Co., Ltd, Suzhou, Jiangsu (CN)

(72) Inventor: Xianglong Li, Jiangsu (CN)

(73) Assignee: SUZHOU HALO BIO-TECH CO., LTD., Suzhou (CN)

( * ) Notice: Subject to any disclaimer, the term of this patent is extended or adjusted under 35 U.S.C. 154(b) by 0 days.

(21) Appl. No.: 15/033,105

(22) PCT Filed: Apr. 14, 2014

(86) PCT No.: PCT/CN2014/075231
§ 371 (c)(1),
(2) Date: Aug. 5, 2016

(87) PCT Pub. No.: WO2015/062208
PCT Pub. Date: May 7, 2015

(65) Prior Publication Data
US 2016/0334426 A1    Nov. 17, 2016

(30) Foreign Application Priority Data

Oct. 30, 2013  (CN) .......................... 2013 1 0529437
Oct. 30, 2013  (CN) .................... 2013 2 0677151 U

(51) Int. Cl.
*G01N 35/00*    (2006.01)
*G01N 35/10*    (2006.01)
(Continued)

(52) U.S. Cl.
CPC ..... *G01N 35/00029* (2013.01); *G01N 33/483* (2013.01); *G01N 35/00009* (2013.01);
(Continued)

(58) Field of Classification Search
CPC . Y10T 436/113332; Y10T 436/114165; Y10T 29/53843; Y10T 436/112499;
(Continued)

(56) References Cited

U.S. PATENT DOCUMENTS 4,218,421 A      8/1980  Mack et al.
2012/0051974 A1*  3/2012  Wang ....................... G01N 1/38
                                                   422/68.1

FOREIGN PATENT DOCUMENTS

CN         1852679 A      10/2006
CN       101487845 A       7/2009
(Continued)

OTHER PUBLICATIONS

European Patent Office, Extended European Search Report for European Patent Application No. 14859130.8; dated Jun. 9, 2017; 9 pages.
(Continued)

*Primary Examiner* — Sally A Merkling
(74) *Attorney, Agent, or Firm* — Perkins Coie LLP; Kenneth H. Ohriner

(57) ABSTRACT

The present invention provides a full-automatic feces analyzer, comprising an automatic controller; at least one sample box for containing a feces sample; a sample box support for placing the sample box; a dilution and stirring unit for adding diluent into the feces sample in the sample box and performing stirring to obtain feces sample liquid; a physical detection unit for performing a physical detection on the feces sample liquid; at least one chemical detection unit for performing a chemical detection on the feces sample liquid, each chemical detection unit comprising a driving roller and a driven roller, a reagent strip roll being wound on the driven roller, an end portion of the reagent strip roll being fixed on the driving roller, and the reagent strip roll comprising a plurality of reagent strips which are abreast (Continued)

distributed and sequentially connected; and a sample sucking and adding unit for sucking the feces sample liquid and delivering the feces sample liquid to the physical detection unit and the chemical detection unit. The full-automatic feces analyzer can perform continuous physical detections and chemical detections to a plurality of feces samples, and the detection efficiency thereof is very high.

10 Claims, 6 Drawing Sheets

(51) Int. Cl.
*G01N 33/483* (2006.01)
*G01N 35/04* (2006.01)
*G01N 1/38* (2006.01)

(52) U.S. Cl.
CPC ....... *G01N 35/00732* (2013.01); *G01N 35/04* (2013.01); *G01N 35/10* (2013.01); *G01N 35/1004* (2013.01); *G01N 1/38* (2013.01); *G01N 2035/00108* (2013.01); *G01N 2035/00534* (2013.01); *G01N 2035/00752* (2013.01); *G01N 2035/0412* (2013.01); *G01N 2035/0443* (2013.01)

(58) Field of Classification Search
CPC ......... G01N 35/10; G01N 2035/00752; G01N 2035/0436; A61B 10/0038; A61B 10/0096; B01F 9/0001; B01F 9/0014; B01F 9/0021; B01L 3/5082
See application file for complete search history.

(56) References Cited

FOREIGN PATENT DOCUMENTS

| | | | |
|---|---|---|---|
| CN | 201935927 | U | 8/2011 |
| CN | 102252968 | A | 11/2011 |
| CN | 202330441 | * | 7/2012 |
| CN | 202330441 | U | 7/2012 |
| CN | 202735339 | U | 2/2013 |
| CN | 202875402 | U | 4/2013 |
| CN | 203535060 | U | 4/2014 |
| EP | 2400305 | A1 | 12/2011 |
| JP | H0835969 | A | 2/1996 |
| JP | H11271321 | A | 10/1999 |
| JP | H111326339 | A | 11/1999 |
| JP | 2012518175 | A | 8/2012 |

OTHER PUBLICATIONS

International Search Report and Written Opinion of International Application No. PCT/CN2014/075231; dated Aug. 1, 2014; 23 pages, includes English translation.
Notice of Reasons for Refusal for Japanese Application No. 2016-526263; dated May 18, 2017; 4 pages (English translation only).

* cited by examiner

FULLY-AUTOMATIC EXCREMENT ANALYZER

CROSS REFERENCE TO RELATED PATENT APPLICATION

The present application is the US national stage of PCT/CN2014/075231 filed on Apr. 14, 2014 which claims the priorities of the Chinese patent applications No. 201310529437.x filed on Oct. 30, 2013 and No. 201320677151.1 filed Oct. 30, 2013, which applications are incorporated herein by reference.

BACKGROUND OF THE PRESENT INVENTION

Field of Invention

The present invention relates to a detection instrument for a hospital, in particular to a full-automatic feces analyzer.

Description of Related Arts

Human feces is a mixture consisting of undigested food, food residues which are digested but not absorbed, secretions of a digestive system, exuviations of digestive tract mucosa, microorganisms, parasites and the like. By detecting the human feces, information about digestive system functions, pathological change, microorganism and parasite infection and the like of a detected person can be obtained. Thus, feces detection (including physical detection and chemical detection) is one of three major conventional detections made by the hospital to patients. At present, feces detection in the hospital is usually manual detection and mainly depends on the skill level and personal experience of laboratory physicians. As a result, a certain influence is caused to examination results and actual situations of detection cannot be very well reflected. In addition, during detection, it is very insanitary.

In order to solve the problem, a Chinese invention patent CN101487845B discloses an automatic detector for a feces sample, which comprises an automatic controller; a sample box for containing a feces sample; a dilution device for adding quantitative diluent into the feces sample; a stirring and blending device for uniformly stirring the diluted feces sample; a detection unit used for detecting the feces sample and comprising a physical detection unit and a chemical detection unit, wherein the physical detection unit comprises a counting cell, the chemical detection unit comprises a chemical detection chamber; and a sample sucking and cleaning device. The automatic detector of a feces sample can automatically perform quantitative dilution, stirring and blending, sample sucking and detection and cleaning, decrease links of contact with an external environment and reduce pollution to the environment and the laboratory. However, since it performs chemical detection on the feces sample through the chemical detection chamber only, the chemical detection cost is comparatively high, an operator is still needed for observation, judgment and reading, the efficiency is very low, and it does not facilitate detection to a plurality of feces samples or multi-item chemical detection to a feces sample.

SUMMARY OF THE PRESENT INVENTION

In view of the disadvantages of the prior art, a purpose of the present invention is to provide a full-automatic feces analyzer which is low in cost and high in detection efficiency.

In order to realize the purpose, the present invention provides a full-automatic feces analyzer, which comprises:

an automatic controller;

at least one sample box for containing a feces sample;

a sample box support for placing the sample box;

a dilution and stirring unit for adding diluent into the feces sample in the sample box and performing stirring to obtain feces sample liquid;

a physical detection unit for performing a physical detection on the feces sample liquid;

at least one chemical detection unit for performing a chemical detection on the feces sample liquid, each chemical detection unit comprising a driving roller and a driven roller, a reagent strip roll being wound on the driven roller, an end portion of the reagent strip roll being fixed on the driving roller, and the reagent strip roll comprising a plurality of reagent strips which are abreast distributed and sequentially connected; and a sample sucking and adding unit for sucking the feces sample liquid and delivering the feces sample liquid to the physical detection unit and the chemical detection unit.

Preferably, the sample box support thereon is provided with a plurality of holding chambers which have upward openings and are used for placing the sample box, an inner wall of each holding chamber thereon is provided with elastic clamping pieces, and after the sample box is placed in the holding chamber, the sample box is in surface contact and interference fit with the elastic clamping pieces.

Further, the full-automatic feces analyzer further comprises a barcode scanner, a barcode is stuck on a rear side of the sample box, a rear side of the sample box support is provided with barcode scanning openings which are provided opposite to the sample boxes, and the barcode scanner scans the barcodes on the sample boxes through the barcode scanning openings.

Preferably, the full-automatic feces analyzer further comprises a character photographing device, a front side of the sample box support is provided with character photographing openings which are provided opposite to the sample boxes, and the character photographing device photographs the feces samples in the sample boxes through the character photographing openings.

Further, the sample sucking and adding unit comprises a first manipulator which is located at the position of the physical detection unit and can move upwards and downwards, and a second manipulator which is located at the position of the chemical detection unit and can move upwards, downwards, leftwards, rightwards, forwards and backwards, the first manipulator thereon is provided with a first sample sucking needle, the first sample sucking needle is connected with a first peristaltic pump, and the physical detection unit comprises a counting cell which is serially connected between the first sample sucking needle and the first peristaltic pump; the second manipulator thereon is provided with a second sample sucking needle, the second sample sucking needle is connected with a second peristaltic pump, the reagent strip thereon is provided with a sample adding area and a protruding portion which is provided opposite to the sample adding area, and during the chemical detection, the second sample sucking needle pierces the protruding portion.

Preferably, the reagent strip is a plastic sealed reagent strip and comprises a supporting plate, a cover plate and a test paper strip, the supporting plate and the cover plate consist of plastic sealing films, edges of the supporting plate and the cover plate are plastic-sealed together, and the test paper strip is sealed between the supporting plate and the cover plate.

Further, the first peristaltic pump and the second peristaltic pump are connected with a cleaning solution bucket, and cleaning solution is contained in the cleaning solution bucket; the first manipulator thereon is provided with a first cleaning needle, the first cleaning needle is connected with the cleaning solution bucket through a first cleaning pump and an end portion of the first cleaning needle extends to an outer wall of the first sample sucking needle; the second manipulator thereon is provided with a second cleaning needle, the second cleaning needle is connected with the cleaning solution bucket through a second cleaning pump and an end portion of the second cleaning needle extends to an outer wall of the second sample sucking needle.

Further, the dilution and stirring unit comprises a third manipulator which can move upwards and downwards, the third manipulator thereon in provided with a stirring motor and a liquid adding needle, the sample box therein is provided with a rotatable sampling spoon, and when the third manipulator is lowered, an output shaft of the stirring motor is coaxially connected with the sampling spoon and the liquid adding needle is inserted into the sample box.

Preferably, the liquid adding needle is connected with a diluent bucket through a third peristaltic pump and diluent is contained in the diluent bucket.

Preferably, a number of the chemical detection units is 5-7, items detected by the reagent strips in each chemical detection unit are different and a plurality of chemical detection units are transversely abreast distributed.

Further, the full-automatic feces analyzer further comprises a photoelectric positioning switch which is located above the reagent strips, the driving roller is connected with a stepping motor, and both the photoelectric positioning switch and the stepping motor are connected with an automatic controller.

As described above, the full-automatic feces analyzer provided by the present invention has the following beneficial effects:

The full-automatic feces analyzer can automatically perform continuous physical detections and chemical detections on a plurality of feces samples, and the detection efficiency thereof is very high; in addition, by completing the chemical detection of the feces samples through the reagent strips, the detection cost is comparatively lower and the full-automatic feces analyzer is suitable for popularization and application.

Figure 1:
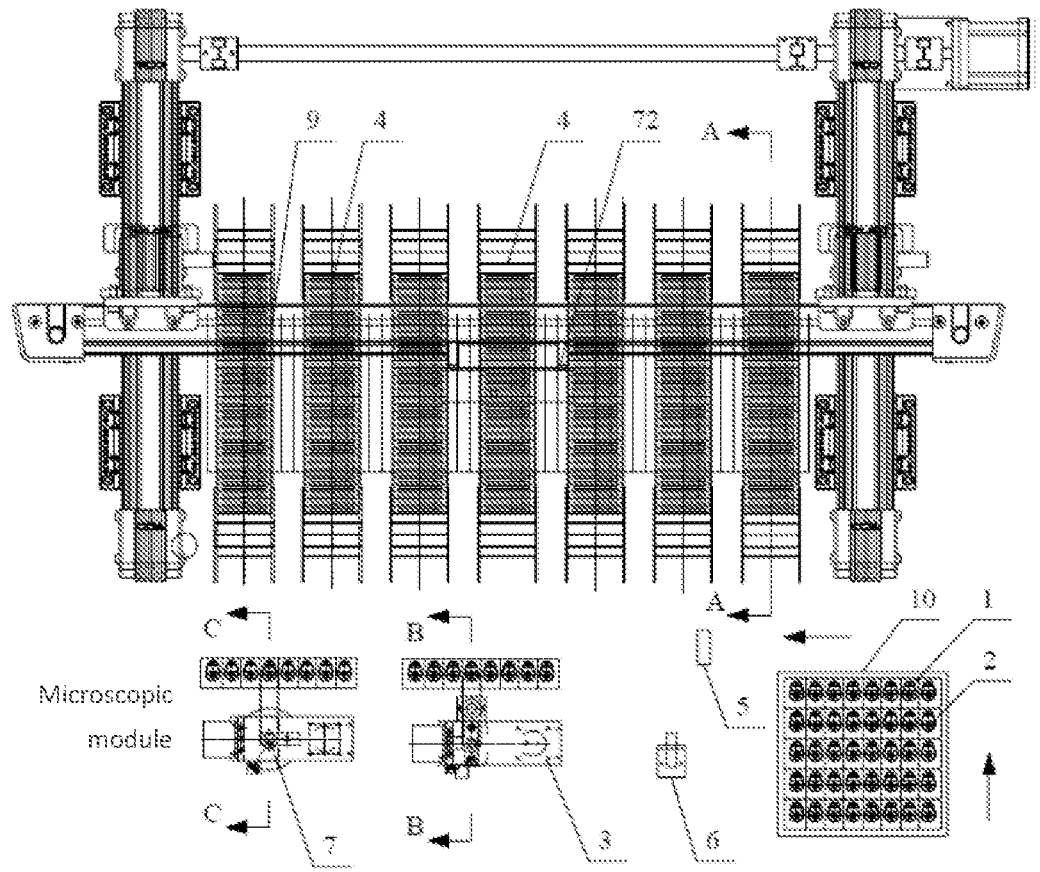
FIG. 1 is a structural schematic view (top view) of the present invention.

DESCRIPTION OF COMPONENT REFERENCE SIGNS 1 sample box
2 sample box support
21 holding chamber
22 elastic clamping piece
23 barcode scanning opening
24 character photographing opening
3 dilution and stirring unit
31 third manipulator
32 stirring motor
33 liquid adding needle
4 chemical detection unit
41 driving roller
42 driven roller
43 reagent strip roll
44 reagent strip
441 sample adding area
442 protruding portion
443 supporting plate
444 cover plate
445 test paper strip
446 detection area
5 barcode scanner
6 character photographing device
7 sample sucking and adding unit
71 first manipulator
72 second manipulator
73 first sample sucking needle
74 first peristaltic pump
75 second sample sucking needle
76 second peristaltic pump
77 cleaning solution bucket
78 first cleaning needle
79 first cleaning pump
710 second cleaning needle
711 second cleaning pump
8 counting cell
9 photoelectric positioning switch
10 limiting switch Detailed Description of the Preferred Embodiments The present invention will be described through specific embodiments. One skilled in the art can easily understand other advantages and effects of the present invention according to the contents disclosed by the description.

It should be understood that structures, scales, sizes and the like illustrated in the drawings annexed to the description are only used for cooperating with the contents disclosed by the description for the sake of understanding and reading by one skilled in the art, are not used for limiting the limited conditions which can be implemented by the present invention, and thus have no technical substantive meanings. Any modification to structures, change to scale relations or adjustment to sizes without influencing the effects which can be produced by the present invention and the purposes which can be achieved by the present invention shall still fall into the range which can be covered by the technical contents disclosed by the present invention. In addition, terms such as "above", "below", "left", "right", "middle" and the like used in the description are only used for facilitating the clearness of description and are not used for limiting the range which can be implemented by the present invention. Change or adjustment to relative relations without substantively changing the technical contents shall also be considered as the range which can be implemented the present invention.

Figure 5:
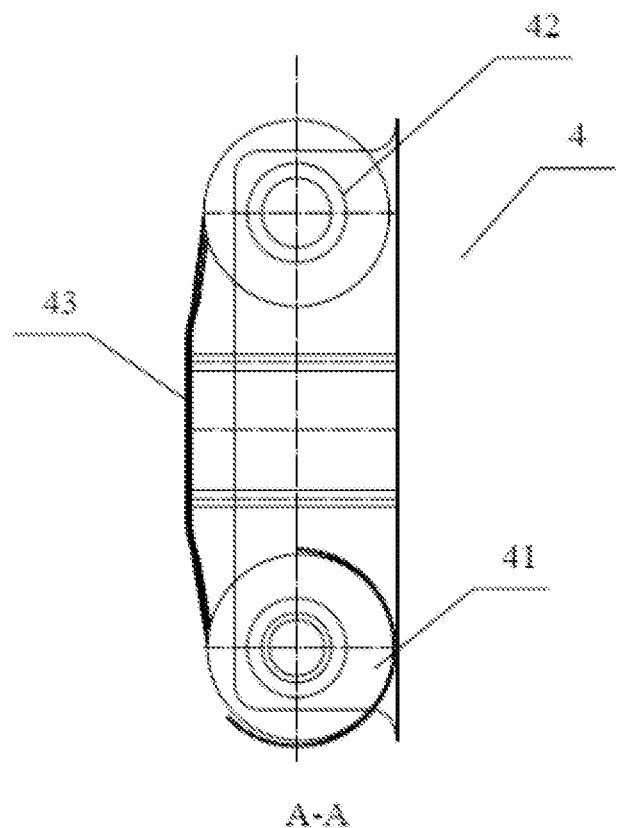
FIG. 5 is an A-A sectional view of FIG. 1.

As shown in FIG. 1, the present invention provides a full-automatic feces analyzer, which comprises:

an automatic controller;

at least one sample box 1 for containing a feces sample;

a sample box support 2 for placing the sample box 1;

a dilution and stirring unit 3 for adding diluent into the feces sample in the sample box 1 and performing stirring to obtain feces sample liquid;

a physical detection unit for performing physical detection on the feces sample liquid;

at least one chemical detection unit 4 for performing chemical detection on the feces sample liquid, each chemical detection unit comprising a driving roller 41 and a driven roller 42, as shown in FIG. 5, a reagent strip roll 43 being wound on the driven roller 42, an end portion of the reagent strip roll 43 being fixed on the driving roller 41, and the reagent strip roll comprising a plurality of reagent strips 44 which are abreast distributed and sequentially connected, preferably, a reagent strip roll 43 therein having at least more than 200 reagent strips 44, more preferably, 200, 500 or 800 servings; and a sample sucking and adding unit 7 for sucking the feces sample liquid and delivering the feces sample liquid to the physical detection unit and the chemical detection unit 4.

In the full-automatic feces analyzer, the feces sample is collected and contained through the sample box 1, then the sample box 1 is delivered through the sample box support 2 into the analyzer for dilution and stirring, subsequently the feces sample liquid is delivered through the sample sucking and adding unit 7 to the physical detection unit for physical detection and to the chemical detection unit 4 for chemical detection, and a plurality of reagent strips 44 are sequentially connected at the position of the chemical detection unit 4, such that continuous detections can be performed on a plurality of feces samples and the detection efficiency is greatly improved. In addition, since the reagent strips 44 are adopted for performing the chemical detection of feces, the detection cost is further reduced. Preferably, the full-automatic feces analyzer further comprises a push-in manipulator, a transfer manipulator and a push-out manipulator connected with the sample box support 2, and the push-in manipulator, the transfer manipulator and the push-out manipulator are in stepping drive, i.e., three sets of stepping motors liner feeding mechanisms are adopted to drive the sample box support 2, wherein the push-in manipulator is used for pushing the sample box support 2 into the analyzer, and the transfer manipulator is used for sequentially transferring the sample box support 2 to the dilution and stirring unit 3 and the physical detection unit; and after all detections are completed, the push-out manipulator pushes the sample box support 2 out of the analyzer.

Preferably, a number of the chemical detection units 4 is 5-7, items detected by the reagent strips 44 in each chemical detection unit 4 are different, a plurality of chemical detection units 4 are transversely abreast distributed, the plurality of chemical detection units 4 are used for simultaneously performing different chemical detections on the feces sample, for example, a reagent strip roll 43 for Fob, rotavirus and *helicobacter pylori* can be selected and used, and during the chemical detection, the sample sucking and adding unit 7 respectively drops sucked feces sample liquid into reagent strips 44 for the three items and thereby the detection of the three items, i.e., Fob, rotavirus and *helicobacter pylori* can be simultaneously performed on the feces sample. In addition, in this embodiment, the full-automatic feces analyzer further comprises two standby chemical detection units 4, no reagent strip roll 43 is installed in the two chemical detection units 4, and the two chemical detection units are empty reagent positions; after a detection personnel is on duty and powers on the analyzer, if the detection personnel finds that a number of residual only Fob reagent strips is only 80 servings (i.e., 80) and a number of feces samples on which Fob detection needs to be performed is 300, the detection personnel can select to install a Fob reagent strip roll in any one of the two standby chemical detection units 4, and thus the Fob detection on all feces samples can be completed; and if a number of Fob reagent strips in the analyzer is 500 servings after the detection personnel powers on the analyzer, the detection can be immediately performed without using the standby chemical detection units 4, and the analyzer does not need to be shut down for changing reagents or samples during the detection.

Figure 2:
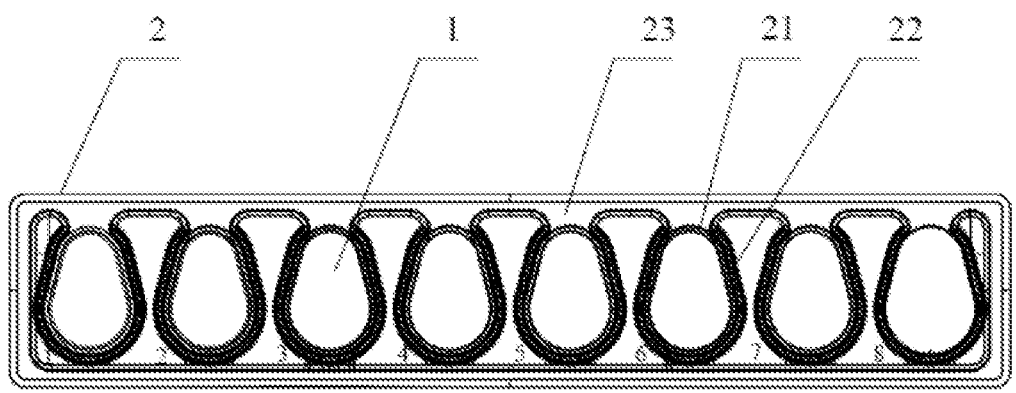
FIG. 2 is a structural schematic view of a sample box support and a sample box in FIG. 1.

Preferably, as shown in FIG. 2, the sample box support 2 thereon is provided with a plurality of holding chambers 21 which have upward openings and are used for placing the sample boxes 1, the holding chambers 21 adapt to the sample boxes 1, an inner wall of each holding chamber 21 thereon is provided with an elastic clamping piece 22, and after the sample box 1 is placed in the holding chamber 21, the sample box 1 is in surface contact and interference fit with the elastic clamping piece 22, such that the sample box 1 is fixed in the holding chamber 21 to prevent the sample box 1 from moving, floating, deviating and the like; and moreover, the outer wall of the sample box 1 is in surface contact with the inner wall of the elastic clamping piece 22, such that the contact area therebetween is increased to guarantee the centering effect of the sample box 1 and further guarantee the smooth proceedings of adding, stirring and sucking the sample in the sample box 1. In addition, in this embodiment, a number of the elastic clamping pieces 22 is two, the two elastic clamping pieces 22 are respectively located at an upper end and a lower end of each holding chamber 21, and the elastic clamping pieces 22 are made of high-elasticity-modulus materials such as aramid fibers, polyethylene fibers, high-modulus glass fibers and high-modulus carbon fibers to increase the wear resistance of the elastic clamping pieces 22, prolong the service life of the elastic clamping pieces 22 and further prolong the service life of the entire sample box support 2.

Figure 3:
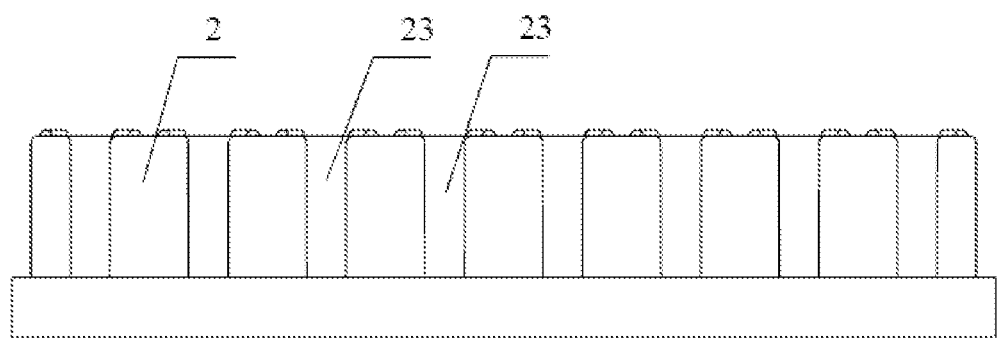
FIG. 3 is a rear view of FIG. 2.
Figure 4:
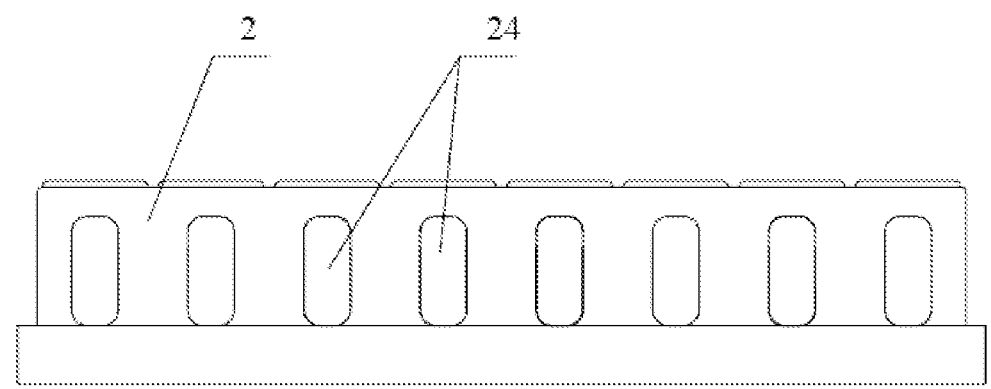
FIG. 4 is a front view of FIG. 2.

Further, the full-automatic feces analyzer further comprises a barcode scanner 5, a barcode is stuck on a rear side of the sample box 1, a rear side of the sample box support 2 is provided with barcode scanning openings 23 which are provided relative to the sample boxes 1, as shown in FIG. 2 and FIG. 3, the barcode scanning openings 23 are communicated with the holding chambers 21 and extend upwardly through the sample box support 2, the barcode scanner 5 scans the barcodes on the sample boxes through the barcode scanning openings. Preferably, the full-automatic feces analyzer further comprises a character photographing device 6, a front side of the sample box support 2 is provided with character photographing openings which are located relative to the sample boxes, as shown in FIG. 2 and FIG. 4, the character photographing openings 24 are communicated with the holding chambers 21, and the character photographing device 6 photographs the feces samples in the sample boxes 1 through the character photographing openings 24 to observe the shapes and colors of the feces samples. The barcode scanner 5 and the character photographing device 6 are longitudinally distributed along a moving direction of the sample box support 2, such that when the transfer manipulator transfers the sample box support 2, each sample box 1 in the sample box support 2 firstly passes through the barcode scanner 5 to read information of a patient, and a subsequent detection result is stored under a directory of the information of the barcode; and thereafter the sample box 1 sequentially passes through the character photographing device 6, the dilution and stirring unit 3 and the physical detection unit.

Figure 6:
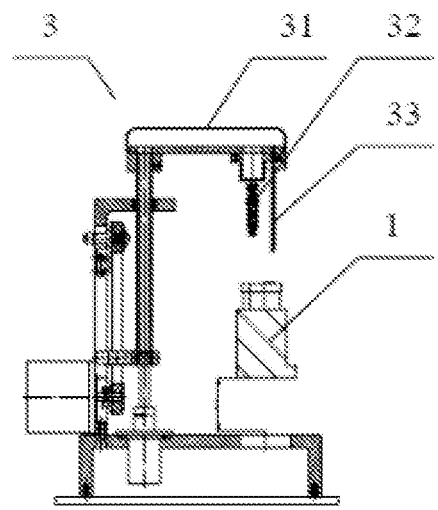
FIG. 6 is a B-B sectional view of FIG. 1.

Further, as shown in FIG. 6, the dilution and stirring unit 3 comprises a third manipulator 31 which can move upwards and downwards, the third manipulator 31 thereon in provided with a stirring motor 32 and a liquid adding needle 33, the sample box 1 therein is provided with a rotatable sampling spoon, and when the third manipulator 3 is lowered, an output shaft of the stirring motor 32 is coaxially connected with the sampling spoon and the liquid adding needle 33 is inserted into the sample box 1. Preferably, the liquid adding needle 33 is connected with a diluent bucket through a third peristaltic pump and diluent is contained in the diluent bucket. In addition, for the structure of the sample box 1, a reference can be made to a Chinese utility model patent CN202735110U; and for the connection structure of the sample box 1 and the stirring motor 32, a reference can be made to a Chinese invention patent CN101487845B. The transfer manipulator transfers the sample box support 2 to the position of the dilution and stirring unit 3, and the sample box 1 on the sample box support 2 is located below the liquid adding needle 33; the third manipulator 31 moves downwards, an input shaft of the stirring motor 32 is coaxially connected with the sampling spoon, and the liquid adding needle 33 is inserted into the sample box 1; the third peristaltic pump rotates and the diluent is added into the sample box 1 through the liquid adding needle 33; and the stirring motor 32 rotates to drive the sampling spoon to rotate, such that the quantitative diluent adding and reasonable stirring of the feces sample are completed.

Figure 7:
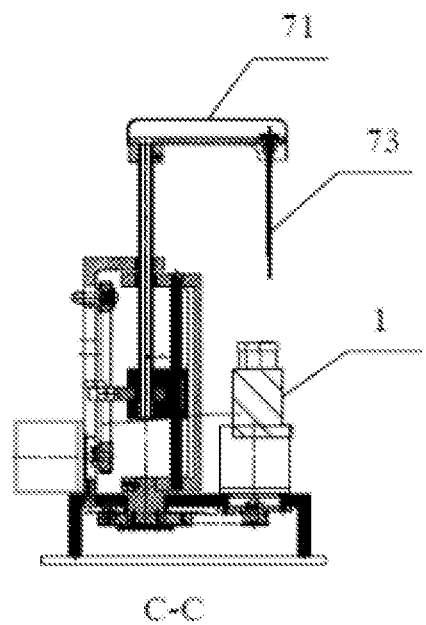
FIG. 7 is a C-C sectional view of FIG. 1.
Figure 8:
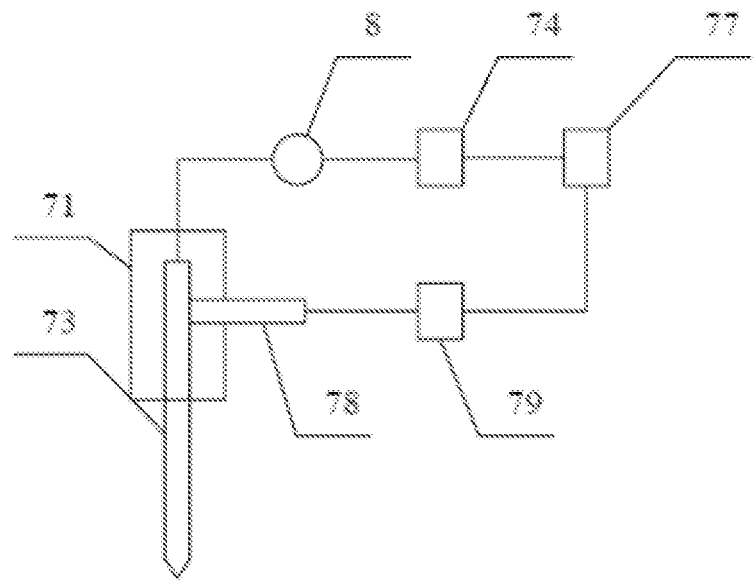
FIG. 8 is a pipe connection diagram of a physical detection unit.
Figure 9:
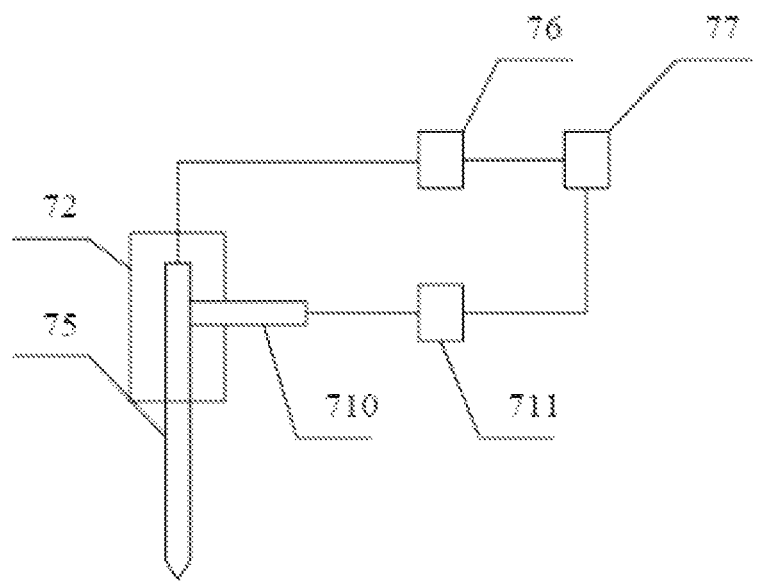
FIG. 9 is a pipe connection diagram of a chemical detection unit.
Figure 10:
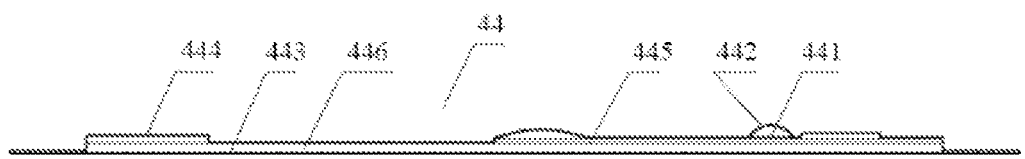
FIG. 10 is a structural schematic view of a reagent strip in the present invention.

Further, as shown in FIG. 7, the sample sucking and adding unit 7 comprises a first manipulator 71 which is located at the position of the physical detection unit and can move upwards and downwards, and a second manipulator 72 which is located at the position of the chemical detection unit and can move upwards, downwards, leftwards, rightwards, forwards and backwards, the first manipulator 71 thereon is provided with a first sample sucking needle 73, the first sample sucking needle 73 is connected with a first peristaltic pump 74, and as shown in FIG. 8, the physical detection unit comprises a counting cell 8 which is serially connected between the first sample sucking needle 73 and the first peristaltic pump 74; the second manipulator 72 thereon is provided with a second sample sucking needle 75, the second sample sucking needle 75 is connected with a second peristaltic pump 76, as shown in FIG. 9, the reagent strip 44 thereon is provided with a sample adding area 441 and a protruding portion 442 which is located opposite to the sample adding area 441, and as shown in FIG. 10, during the chemical detection, the second sample sucking needle pierces the protruding portion 442. The second manipulator 72 is a three-dimensional manipulator, can move 800 mm in an X direction, can move 300 mm in a Y direction and can move 100 mm on a Z direction.

Figure 11:
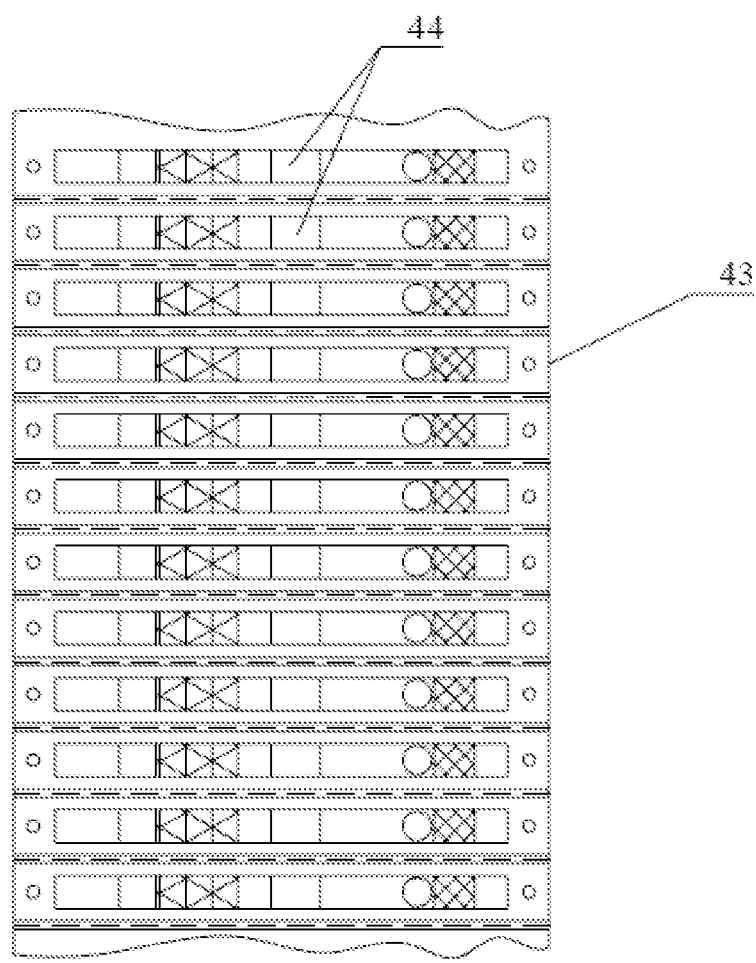
FIG. 11 is a structural schematic view of a reagent strip roll in the present invention.

In addition, in order to further reduce the detection cost, for the sake of reduction of the cost of the reagent strips 44 in the present invention, the reagent strips 44 are designed to be plastic sealed reagent strips 44, as shown in FIG. 10 and FIG. 11, each plastic sealed reagent strip 4 comprises a supporting plate 443, a cover plate 444 and a test paper strip 445, the supporting plate 443 and the cover plate 444 consist of plastic sealing films, edges of the supporting plate 443 and the cover plate 444 are plastic-sealed together, the test paper strip 445 is sealed between the supporting plate 443 and the cover plate 444, and the test paper strip 445 thereon is further provided with a detection area 446. Since the supporting plate 443 and the cover plate 444 consist of the plastic sealing films, the manufacturing cost of the reagent strips 44 is effectively reduced and the economic benefit is improved. Moreover, since the edges of the supporting plate 443 and the cover plate 444 are plastic-sealed together and the test paper strip 445 is sealed between the supporting plate 443 and the cover plate 444, the dryness of the reagent strips 44 is effectively guaranteed, such that the reagent strips 44 can be exposed in air for a long time without being damped. Preferably, two adjacent plastic sealed reagent strips 44 are connected through a tear line, such that a single plastic sealed reagent strip 44 can be conveniently torn off and used separately to satisfy demands of different places.

During the physical detection, the sample box 1 which contains the feces sample liquid is located below the first sample sucking needle 73, the first manipulator 71 moves downwards, the first sample sucking needle 73 is inserted into the sample box 1, the first peristaltic pump 74 rotates forwardly, and the feces sample liquid is sucked out from the sample box 1 and enters the counting cell 8 through the first sample sucking needle 73 to perform a microscopic detection; and a microscopic examination module has a pre-adjustment focusing function and the counting cell 8 can realize multi-point movement in a horizontal direction. During the chemical detection, the second manipulator 72 moves to enable the second sample sucking needle 75 to be inserted into the sample 1, the second peristaltic pump 76 rotates forwardly and the feces sample liquid is sucked from the sample box 1 into the second sample sucking needle 75; and the second manipulator 72 moves again to enable the second sample sucking needle 75 to be inserted into the protruding portion 442 on the reagent strip 44, the second peristaltic pump 76 rotates reversely, and the feces sample liquid in the second sample sucking needle 75 is dropped onto the sample adding area 441 of the reagent strip 44 to perform the chemical detection. In this embodiment, the second manipulator 72 thereon is provided with a photographing camera which is used for photographing the reagent strip 44 after reactions, the automatic controller then controls a judgment and reading software to judge and read the obtained photo to make a qualitative conclusion to obtain a chemical detection result, so as to prevent errors from being caused by artificial judgment and reading, improve the detection accuracy and speed and realize an automatic detection. Preferably, a photoelectric sensor is provided at the position of the physical detection unit and is used for confirming the position of the sample box 1.

After the detection of the feces sample liquid is completed, detection shall not be performed on next feces sample liquid until the inner walls and outer walls of the first sample sucking needle 73 and the second sample sucking needle 75 are cleaned. In this embodiment, a cleaning structure is as shown in FIG. 8 and FIG. 9, the first peristaltic pump 74 and the second peristaltic pump 75 are connected with a cleaning solution bucket 77, and cleaning solution is contained in the cleaning solution bucket 77; the first manipulator 71 thereon is provided with a first cleaning needle 78, the first cleaning needle 78 is connected with the cleaning solution bucket 77 through a first cleaning pump 79 and an end portion of the first cleaning needle 78 extends to an outer wall of the first sample sucking needle 73; and the second manipulator 72 thereon is provided with a second cleaning needle 710, the second cleaning needle 710 is connected with the cleaning solution bucket 77 through a second cleaning pump 711 and an end portion of the second cleaning needle 710 extends to an outer wall of the second sample sucking needle 75.

After the physical detection is completed, the first peristaltic pump 74 rotates reversely, and the cleaning solution in the cleaning solution bucket 77 is sucked inside and enters the first sample sucking needle 73 through the counting cell 8 to clean the inner walls of the counting cell 8 and the first sample sucking needle 73; the first cleaning pump 79 rotates, and the cleaning solution is sucked inside by the first cleaning needle 78 and flows downwards along the outer wall of the first sample sucking needle 73 to clean the outer wall of the first sample sucking needle 73. After the chemical detection is completed, the second peristaltic pump 76 rotates reversely, and the cleaning solution in the cleaning solution bucket 77 is sucked into the second sample sucking needle 75 to clean the inner wall of the second sample sucking needle 75; the second cleaning pump 711 rotates, and the cleaning solution is sucked inside by the second cleaning needle 710 and flows downwards along the outer wall of the second sample sucking needle 75 to clean the outer wall of the second sample sucking needle 75. Waste liquid obtained after cleaning the first sample sucking needle 73 and the second sample sucking needle 75 flows into a waste liquid bucket to facilitate centralized discharge of the waste liquid, and the waste liquid bucket therein is provided with a liquid level switch which is used for realizing an upper limit alarm, i.e., when a liquid level of liquid in the waste liquid bucket is higher than the liquid level switch, the liquid level switch is triggered and the automatic controller gives out an alarm according to a trigger signal. In addition, the diluent bucket and the cleaning solution bucket 77 therein are respectively provided with a liquid level switch which is used for a lower limit alarm, i.e., when a liquid level of the diluent in the diluent bucket is lower than the liquid level switch or a liquid level of the cleaning solution in the cleaning solution bucket 77 is lower than the liquid level switch, the liquid level switch is triggered and the automatic controller gives out an alarm according to a trigger signal.

Preferably, when the first sample sucking needle 73 and the second sample sucking needle 75 are cleaned, the automatic controller controls the first peristaltic pump 74, the second peristaltic pump 76, the first cleaning pump 79 and the second cleaning pump 711 to rotate intermittently such that a section of cleaning solution, a section of air, a section of cleaning solution, a section of air . . . are distributed at intervals in a cleaning pipe, the cleaning solution is delivered out intermittently, internal pressure of the pipe is increased under the effect of air to enable the cleaning solution to flush the inner wall and outer wall of the first sample sucking needle 73 and the inner wall and outer wall of the second sample sucking needle 75 in a blasting manner, the flushing force is great and thus the cleaning effect is guaranteed.

Further, the full-automatic feces analyzer further comprises a photoelectric positioning switch 9 which is located above the reagent strips 44, the driving roller 41 is connected with a stepping motor, and both the photoelectric positioning switch 9 and the stepping motor are connected with an automatic controller; and the stepping motor drives the driving roller 41 to roll in a stepping manner, and under the effect of the photoelectric positioning switch 9, the reagent strip roll 43 is guaranteed to advance once according to a unit of one reagent strip 44 when the roller rotates once.

Before the full-automatic analyzer provided by the present invention works, the push-in manipulator stays at the forefront of the analyzer, the transfer manipulator stays on the leftmost side of the analyzer, the third manipulator 31 stays at the topmost position, the first manipulator 71 stays at the topmost position of the physical detection unit, the second manipulator 72 stays at the topmost position of the reagent strip 44, a reagent cassette stays at an initial position or a memory position, and the push-out manipulator stays at the rear end of the analyzer. During working, a plurality of sample boxes 1 are manually put into the sample box support 2, the sample boxes 1 therein respectively contain feces samples of different patients, as shown in FIG. 1, the push-in manipulator pushes the sample box support 2 into the analyzer, and from the angle of view of FIG. 1, the sample box support 2 enters the analyzer from front to rear; when the sample box support 2 touches a limiting switch 10 at the rear end of the analyzer, the push-in manipulator stops moving, and the transfer manipulator transversely transfers the sample box support 2 from right to left in a stepping manner to sequentially pass through the barcode scanner 5, the character photographing device 6, the dilution and stirring unit 3 and the physical detection unit; and in a process of continuous stepping transfer, the feces sample liquid at the position of the physical detection unit is subjected to the physical detection and chemical detection, and simultaneously the feces sample at the position of the dilution and stirring unit 3 is diluted and stirred, such that the analyzer can continuously perform detections on a plurality of different feces samples, the detection speed can reach 120 feces samples per hour and thus the detection efficiency is greatly improved. Preferably, the analyzer is further equipped with a computer and a printer, and the printer is used for printing the detection result of a feces sample.

To sum up, the present invention effectively overcomes various disadvantages in the prior art and thus has a great industrial utilization value.

The above-mentioned embodiments are just used for exemplarily describing the principle and effect of the present invention instead of limiting the present invention. One skilled in the art can make modifications or variations to the above-mentioned embodiments without departing from the spirit and the range of the present invention. Therefore, all equivalent modifications or variations made by those who have common knowledge in the art without departing from the spirit and technical concept disclosed by the present invention shall be still covered by the claims of the present invention.

What is claimed is:

1. An automatic feces analyzer, comprising:
an automatic controller;
at least one sample box for containing a feces sample;
a sample box support for supporting the sample box;
a dilution and stirring unit for adding diluent into the feces sample in the
sample box and stirring the feces sample and diluent to obtain feces sample liquid;
a physical detection unit for performing a physical detection on the feces sample liquid,
at least one chemical detection unit for performing a chemical detection on the feces sample liquid, each chemical detection unit comprising a driving roller and a driven roller, a reagent strip roll being wound on the driven roller, an end portion of the reagent strip roll being fixed on the driving roller, and the reagent strip roll comprising a plurality of reagent strips sequentially connected; and a sample sucking and adding unit for sucking the feces sample liquid and delivering the feces sample liquid to the physical detection unit and the chemical detection unit;

the sample sucking and adding unit comprises a first manipulator which is located at the position of the physical detection unit and can move upwards and downwards, and a second manipulator which is located at the position of the chemical detection unit and can move upwards, downwards, leftwards, rightwards, forwards and backwards, the first manipulator thereon is provided with a. first sample sucking needle, the first sample sucking needle is connected with a first peristaltic pump, and the physical detection unit comprises a counting cell which is serially connected between the first sample sucking needle and the first peristaltic pump; the second manipulator thereon is provided with a second sample sucking needle, the second sample sucking needle is connected with a second peristaltic pump, the reagent strip having a test paper strip sealed by a sealing film in a protruding portion, the second sample sucking needle movable by the second manipulator from a first position above the protruding portion, to a second position wherein a lower end of the second sample sucking needle is pierced through the sealing film and into the protruding portion.

2. The feces analyzer according to claim 1, characterized in that the sample box support has a plurality of holding chambers which have upward openings for receiving the sample box, an inner wall of each holding chamber having elastic clamping pieces providing an interference fit with the sample box.

3. The feces analyzer of claim 1 further comprising a barcode scanner, a barcode on a rear side of the sample box, and barcode scanning openings in a rear side of the sample box to allow the bar code scanner to scan the barcodes on the sample boxes through the barcode scanning openings.

4. The feces analyzer of claim 1 further including a character photographing device, and character photographing openings in a front side of the sample box support opposite to the sample boxes, to allow the character photographing device to photograph the feces samples in the sample boxes through the character photographing openings.

5. The feces analyzer according to claim 1, characterized in that the first peristaltic pump and the second peristaltic pump are connected with a cleaning solution bucket, and cleaning solution is contained in the cleaning solution bucket; the first manipulator is provided with a first cleaning needle, the first cleaning needle is connected with the cleaning solution bucket through a first cleaning pump and an end portion of the first cleaning needle extends to an outer wall of the first sample sucking needle, the second manipulator is provided with a second cleaning needle, the second cleaning needle is connected with the cleaning solution bucket through a second cleaning pump and an end portion of the second cleaning needle extends to an outer wall of the second sample sucking needle.

6. The feces analyzer according to claim 1, characterized in that the dilution and stirring unit comprises a third manipulator which can move upwards and downwards, the third manipulator in provided with a stirring motor and a liquid adding needle, the sample box is provided with a rotatable sampling spoon, and when the third manipulator is lowered, an output shaft of the stirring motor is coaxially connected with the sampling spoon and the liquid adding needle is inserted into the sample box.

7. The feces analyzer according to claim 6, characterized in that the liquid adding needle is connected with a diluent bucket through a third peristaltic pump and diluent is contained in the diluent bucket.

8. The feces analyzer according to claim 1 having 5-7 chemical detection units, items detected by the reagent strips in each chemical detection unit are different and a plurality of chemical detection units are transversely abreast distributed.

9. The feces analyzer according to claim 1 further comprising a photoelectric positioning switch located above the reagent strips, the driving roller is connected with a stepping motor, and both the photoelectric positioning switch and the stepping motor are connected with an automatic controller.

10. An automatic feces analyzer, comprising:
an automatic controller;
at least one sample box for containing a feces sample;
a sample box support for supporting the sample box;
a dilution and stirring unit for adding diluent into the feces sample in the
sample box and stirring the feces sample and diluent to obtain feces sample liquid;
a physical detection unit for physically detecting the feces sample liquid;
one or more chemical detection units for performing a chemical detection on the feces sample liquid, each chemical detection unit comprising a reagent strip roll having a plurality of reagent strips;
a sample adding unit for delivering the feces sample liquid to the physical detection unit and the chemical detection unit, the sample adding unit having a first manipulator adjacent to the physical detection unit, the first manipulator having a first sampling needle connected to a first peristaltic pump for providing the feces sample liquid to the physical detection unit, the sample adding unit also having a second manipulator having a second sampling needle connected to a second peristaltic pump for providing the feces sample liquid to the chemical detection unit;
the reagent strip having a test paper strip sealed in a protruding portion by a sealing film, the second sampling needle movable by the second manipulator from a first position above the protruding portion, to a second position wherein a lower end of the second sampling needle is pierced through the sealing film and into the protruding portion.

* * * * *